US009707258B2

(12) United States Patent
Aubert-Jacquin et al.

(10) Patent No.: US 9,707,258 B2
(45) Date of Patent: Jul. 18, 2017

(54) **BIOCONVERSION OF MILK WITH *BIFIDOBACTERIUM BREVE* FOR TREATMENT OF ALLERGIC MANIFESTIONS IN INFANTS**

(75) Inventors: Cécile Aubert-Jacquin, Lyons (FR); Francis Lecroix, Godewaersvelde (FR); Emmanuel Perrin, Boeschepe (FR); Valérie Petay, Heuvelland (BE)

(73) Assignee: Compagnie Gervais Danone, Paris (FR)

( * ) Notice: Subject to any disclaimer, the term of this patent is extended or adjusted under 35 U.S.C. 154(b) by 970 days.

(21) Appl. No.: 12/680,779

(22) PCT Filed: Oct. 2, 2008

(86) PCT No.: PCT/FR2008/001372
§ 371 (c)(1),
(2), (4) Date: Mar. 30, 2010

(87) PCT Pub. No.: WO2009/074754
PCT Pub. Date: Jun. 18, 2009

(65) Prior Publication Data
US 2010/0221226 A1 Sep. 2, 2010

(30) Foreign Application Priority Data
Oct. 3, 2007 (FR) .................................... 07 06925

(51) Int. Cl.
| | |
|---|---|
| *A61K 35/20* | (2006.01) |
| *A61K 35/744* | (2015.01) |
| *A61K 35/745* | (2015.01) |
| *A23C 9/123* | (2006.01) |
| *A23C 21/02* | (2006.01) |
| *A23L 33/00* | (2016.01) |
| *A23L 33/135* | (2016.01) |

(52) U.S. Cl.
CPC .......... *A61K 35/745* (2013.01); *A23C 9/1234* (2013.01); *A23C 21/026* (2013.01); *A23L 33/135* (2016.08); *A23L 33/40* (2016.08); *A61K 35/20* (2013.01); *A61K 35/744* (2013.01); *A23V 2002/00* (2013.01); *A23Y 2300/29* (2013.01)

(58) Field of Classification Search
CPC .. A61K 2300/00; A61K 35/742; A61K 35/74; A61K 31/702; A61K 31/4178; A61K 31/496; A61K 31/704; A61K 31/7048; A61K 35/36; A61K 45/06; A61K 31/43; A61K 31/431; A61K 9/0014; A61K 35/744; A61K 35/745; A61K 31/10; A61K 31/437; A61K 31/715; A61K 35/741; A61K 9/4825; A61K 2039/52; A61K 2039/55594; A61K 31/202; A61K 35/20; A61K 31/198; A61K 31/375; A61K 33/03; A23V 2002/00; A23V 2200/304; A23V 2200/3204; A23C 21/026; A23C 9/1234; A23L 33/135; A23L 33/40; A23Y 2300/29
See application file for complete search history.

(56) References Cited

U.S. PATENT DOCUMENTS

| | | | |
|---|---|---|---|
| 7,410,653 B1 * | 8/2008 | Blareau et al. ............... | 424/520 |
| 8,119,379 B2 * | 2/2012 | Blareau et al. ............... | 435/170 |
| 2005/0175630 A1 * | 8/2005 | Raz .................... | A61K 39/0208 424/203.1 |
| 2005/0180963 A1 * | 8/2005 | Adams .................. | A23K 1/009 424/93.45 |

OTHER PUBLICATIONS

International Search Report and Written Opinion for Appl. No. PCT/FR2008/001372 mailed May 28, 2009.
*Antiallergic Agent for Treating and Preventing Allergy Such as Atopic Dermatisis—Comprises Enterobacterium Like Bifido Bacterium, Lactobacillus Acidophilus*, WPI World Patent Inf. Jan. 1900,, 1 page.
Hoarau, C. et al., *Supernantant of Bifidobacterium Breve Induces Dendritic Cell Maturation, Activation, and Survival Through a Tool-Like Receptor 2 Pathway*, J. Allergy Clin Immunol, vol. 117, No. 3, Mar. 2006, pp. 696-702.
Kirjavainen, P. V. et al., *Abberant Composition of Gut Microbiota of Allergic Infants: a Target of Bifidobacterial Therapy at Weaning?*, GUT, British Medical Association, London, vol. 51, No. 1, (2002), pp. 51-55.
Matsumoto, S. et al., *Preventive Effects of Bifidobacterium- and Lactobacillus-Fermented Milk on the Development of Inflammatory Bowel Disease in Senescence-Accelerated Mouse P1/Yit Strain Mice*, Digestion, Basel, vol. 64, No. 2, (2001), pp. 92-99.
Menard, S. et al., *Lactic Acid Bacteria Secrete Metabolites, Retaining Anti- Inflammatory Properties After Intestinal Transport*, GUT, British Medical Association, London, vol. 63, No. 6, (2004), pp. 821-828.
Mullie, C. et al., *Partial Characterization of Bifidobacterium Breve C50 Cell-Free Whey Compounds Including Modifications to the Intestinal Microflora*, J.Dairy Sci., vol. 85, No. 6, (2002), pp. 1383-1389.
Nakamura, Y. et al., *Agent for preventing and/or Treating Allergies, Comprises Bifidobacterium, or its Processed Substance Chosen From e.g. Culture, Concentrate and Paste of Bifidobacterium, as an Active Ingredient* Derwent/WPI, Jan. 1900, 2 pages.

(Continued)

*Primary Examiner* — Debbie K Ware
(74) *Attorney, Agent, or Firm* — Alston & Bird LLP

(57) ABSTRACT

The present invention relates to the use of a *Bifidobacterium* strain for the preparation of compositions, in particular of an infant formula, intended for the prevention and/or treatment of allergic-type manifestations. These compositions are obtained from a *Bifidobacterium* culture, without hydrolyzing milk proteins. The bacteria, which preferably belong to the species *Bifidobacterium breve*, may be killed or removed from the composition during the process.

5 Claims, 3 Drawing Sheets

(56) References Cited

OTHER PUBLICATIONS

Peng, S. et al., *Antiallergic Effect of Milk Fermented With Lactic Acid Bacteria in a Murine Animal Model*, J. Agric. Food Chem., vol. 55, No. 13, (2007), pp. 5092-5096.

Prescott, S. L. et al., *Clinical Effects of Probiotics Are Associated with Increased Interferon-γ Responses in Very Young Children With Atopic Dermatitis*, Clin Exp Allergy, vol. 35, No. 12, (2005), pp. 1557-1564.

Prioult, G. et al., *Allergencity of Acidic Peptides From Bovine βlactoglobulin is Reduced by Hydrolysis with Bifidobacterium Lactis NCC362 Enzymes*, International Dairy Journal, Elsevier Applied Science, vol. 15, No. 5, (2005), pp. 439-448.

\* cited by examiner

BIOCONVERSION OF MILK WITH *BIFIDOBACTERIUM BREVE* FOR TREATMENT OF ALLERGIC MANIFESTIONS IN INFANTS

FIELD OF THE INVENTION

The present invention relates to a method for preparing compositions, in particular an infant formula, which make it possible to reduce allergic-type manifestations. These compositions are obtained from a *Bifidobacterium* culture, without hydrolyzing milk proteins.

BACKGROUND OF THE INVENTION

For several decades, the incidence of allergic diseases has been on the increase in industrialized countries. Thus, it is nowadays estimated that 20% of the population of developed countries is affected by a form of allergy such as asthma, atopic dermatitis, or other forms of manifestations. This high incidence today places allergy as a public health problem and hence numerous research studies have been undertaken in order to try to provide solutions which make it possible to limit the development of these pathologies. These research studies have made it possible to identify the first 2 years of life as a critical period in the establishment of the disease, and in particular by phases for sensitization to allergens, children developing sensitization during this period being at a greater risk of subsequently developing an allergy. Moreover, the role of the intestinal flora in the onset of the allergy has also started to be revealed. Indeed, the establishment of the intestinal flora in children determines the development of the mucosal immune system (Prescott et al., 2005), and the modes of establishment of the flora could influence the immune orientation toward oral orientation or on the contrary toward sensitization (Kalliomaki et al., 2001; Sudo et al., 1997).

Allergy is defined more precisely as a hypersensitivity reaction involving an immune mechanism (Johansson et al., 2001). This hypersensitivity causes reproducible symptoms, triggered by exposure to an antigen, at a dose that is normally tolerated in normal subjects. The antigens causing an allergic reaction, the allergens, are very diverse in nature, of the food, air or animal type, and the like. Likewise, the symptoms observed vary widely, and are mainly of the skin, digestive or respiratory type. The strategies proposed for preventing the allergy have the objective of reducing the incidence of new cases of allergy (primary prevention), or of limiting the duration and the progression of the allergy when it is established (secondary prevention).

In infants, the most frequent allergies are food allergies, and in particular cow's milk protein allergy (CMPA). This risk is all the more great in atopic subjects (high allergic risk children, in particular due to a known allergic heredity), which justifies a strategy, in these children, of dietary intervention during early childhood. Prolonged (>6 months) exclusive maternal breastfeeding, combined with gradual dietary diversification, is the reference solution, breastfeeding having a potentially protective effect toward the appearance of an allergic disease (Host and Halken, 2005). For at-risk children who don't have the advantage of maternal breastfeeding, another strategy involving denaturation of cow's milk proteins by partial or extensive hydrolysis, or their replacement with other animal or plant proteins, is recommended (Host et al., 1999). Yet, the preventive efficacy of these solutions remains controversial (Osborn and Sinn, 2006a; Osborn and Sinn, 2006b), and the hydrolysis process has the consequence of damaging the organoleptic quality and the nutritional quality of the proteins, causing refusal in some children. In France, the hydrolyzed formulas are furthermore subject to specific legislation limiting their distribution to the pharmacy network exclusively, which is an additional constraint for parents of these at-risk children.

The anti-allergenic effect of fermented milks has been described, from a mechanistic angle, by Peng et al. The products studied are acidified probiotic fermented milks (pH=3.7) of the "yogurt" type. In the model presented, the effect is due to the double component of the product tested: fermentation and keeping the ferments alive (>$10^9$ cfu/ml). Five different types of ferments were tested (3 *lactobacilli*, 1 *Streptococcus thermophilus* MC and 1 *Bifidobacterium longum*) and the authors observed widely varying effects dependent on the strain used. In this animal model, the most remarkable effects were observed for the strains of *lactobacilli* tested. Moreover, the effects observed are purely of the immunological type, and not directly linked to clinical observations on the symptomatology of the allergic type (Peng et al., 2007). It should be noted, moreover, that all probiotic strains are not compatible with infant nutrition, D-lactic acid being nonmetabolizable by breastfeeding infants.

Terpend et al. studied more specifically the properties of a milk fermented by *Bifidobacterium breve* and *Streptococcus thermophilus*. The results of this study show an effect of strengthening of the intestinal barrier against milk proteins. However, these authors failed to demonstrate a direct anti-allergenic effect of such a fermented milk (Terpend et al., 1999).

In this context, the inventors have developed formulations suitable for infant nutrition, which at least partially overcome the disadvantages of the products described in the prior art, which makes it possible to provide a different approach in the dietary management of children having an allergic risk.

SUMMARY OF THE INVENTION

The approach chosen to provide a benefit consists in directly regulating the establishment of the flora and of the intestinal immune system of the child through immuno-modulatory active compounds derived from bioconversion or from fermentation by a *Bifidobacterium* strain. The results presented in the experimental section below demonstrate the direct benefits on the allergic symptomatology.

The present invention therefore relates, firstly, to the use of a *Bifidobacterium* strain for the preparation of a composition intended for the prevention and/or treatment of allergic-type manifestations. According to a preferred embodiment of the invention, the *Bifidobacterium* strain used is derived from the human intestinal flora. Preferably still, this strain belongs to the species *Bifidobacterium breve*. A strain that is particularly suitable for carrying out the present invention is the strain BbC50, deposited on 31 May 1999 by Compagnie Gervais Danone, at the Collection Nationale de Cultures de Microorganismes (CNCM), under the number I-2219.

DETAILED DESCRIPTION

Figure 1:
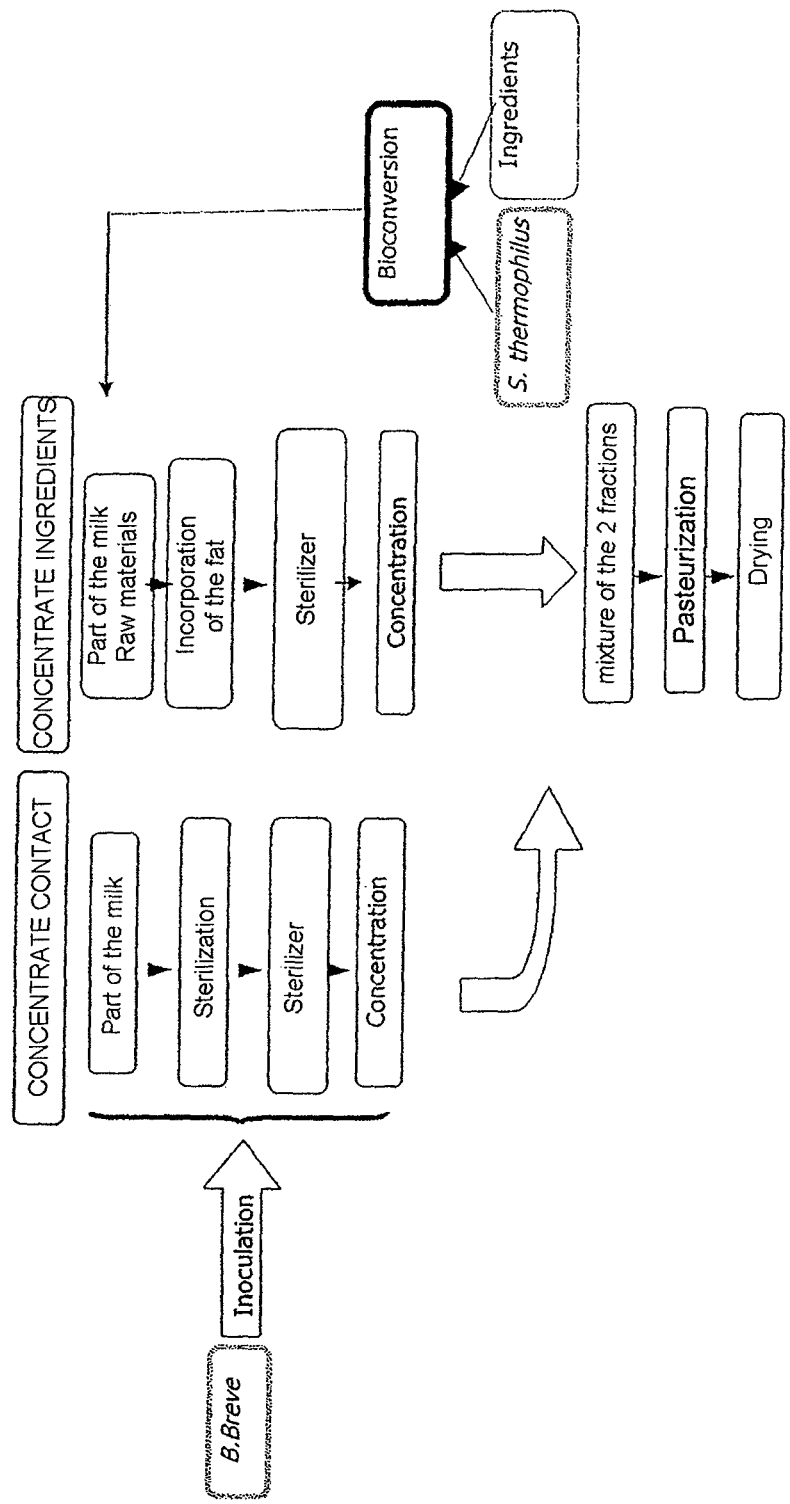
FIG. 1: representation scheme of the preparation of the compositions according to the invention.

A method for preparing a composition intended for the prevention and/or treatment of allergic manifestations in accordance with the invention advantageously comprises a step for fermenting a milk substrate in the presence of the *Bifidobacterium* strain. This step for fermenting a milk substrate in the presence of the abovementioned *Bifidobacterium* strain may be carried out under aerobic or anaerobic conditions.

The expression "milk substrate" is understood to mean here an aqueous medium comprising at least one whey protein fraction and lactose. Where appropriate, the whey proteins may be hydrolyzed and/or enriched with native lactalbumin. Whey permeate may also be incorporated into the milk substrate. By way of nonlimiting examples of milk substrates, there may be mentioned milk, a milk concentrate, an infant milk food base, a yogurt base and the like.

In a preferred embodiment of the invention, the method for preparing a composition intended for the prevention and/or treatment of allergic manifestations in accordance with the invention comprises a step for the bioconversion of a milk substrate by the *Bifidobacterium* strain, carried out under conditions unfavorable for the production of acid by said strain, as described in application WO 2001/001785. This bioconversion, which corresponds to a nonacidifying or weakly acidifying fermentation, also allows the production of active metabolites. Details on the conditions of this particular fermentation are indicated below.

The expression "conditions unfavorable for the production of acid by *Bifidobacterium*" defines conditions under which the acidification of the medium by *Bifidobacterium* does not exceed 0.5 pH units in 8 hours of incubation for an initial inoculation greater than $1 \times 10^7$ CFU per ml. They can be easily determined by persons skilled in the art with the aid of simple tests, by varying in particular the aeration of the culture medium, its osmotic pressure and/or the culture temperature, and by measuring the pH at the start and at the end of the culture.

For a large number of *Bifidobacterium* strains, such conditions may in particular be obtained by:
using a bacterial population derived from an inoculum at a stage after the exponential growth phase;
maintaining under aerobic conditions, for example with stirring;
maintaining the medium at an osmotic pressure corresponding to a water activity (WA) of 0.93 to 0.97;
maintaining at a temperature of 40 to 48° C.;
and combinations of these different conditions.

In this embodiment of the invention, the milk substrate and the bifidobacteria may be brought into contact at the rate of $10^7$ to $10^9$ CFU per ml of milk substrate, and the final population of bifidobacteria at the end of the bioconversion reaction may be between $10^5$ and $10^9$ CFU per ml of product.

The pH of the milk substrate during the bringing into contact with the bacteria is preferably 6.0 to 7 and the pH of the product at the end of the bioconversion reaction is preferably 5.8 to 7.

Depending on the conditions used, the contact time between the milk substrate and the bacteria for such a bioconversion step may be between 4 and 24 hours.

Of course, in a method in accordance with the invention, the bioconversion and fermentation steps described above are not mutually exclusive. For example, such a method may comprise a step of bioconversion (that is acidifying to a greater or lesser degree) of a milk substrate by *Bifidobacterium*, followed by a step of acidic fermentation by this same bacterium. Alternatively, the two reactions may be carried out in parallel, on two different milk substrates, the products of the two reactions then being combined in the final anti-allergic composition.

Depending on the nature of the antiallergic composition which it is desired to obtain, various additional treatments may be applied to the product of the bioconversion and/or fermentation of the milk substrate by the bifidobacteria. In particular, a step of sterilization and/or of separation of the bifidobacteria may be advantageously envisaged at the end of the fermentation or bioconversion step, in particular in order to obtain products with a long shelf life. Likewise, various filtration, dehydration or chromatography steps may be carried out depending on the nature of the final composition which it is desired to obtain.

Examples of products which can be used for the preparation of a composition intended for the prevention and/or treatment of allergic manifestations, in accordance with the present invention, are described in particular in applications WO 2001/001785 (product used in example 1 below), WO 2004/093898 and WO 2004/093899 (example 2), and WO 2006/040485. Of course, mixtures of these products may also be used in accordance with the invention.

Where appropriate, a composition obtained by a method of the invention may comprise, in addition to the product of the fermentation or bioconversion of a milk substrate by a *Bifidobacterium* strain, a mass resulting from the fermentation of a milk substrate by a *Streptococcus thermophilus* strain, for example by the strain ST065, deposited on 23 Aug. 1995 by Compagnie Gervais Danone, at the Collection Nationale de Cultures de Microorganismes (CNCM), under the number I-1620. A composition obtained according to the present invention may advantageously contain a fraction obtained by a method as described in application WO 96/06924.

According to a preferred embodiment of the invention, the composition obtained is a health food (or functional food), that is to say a food or food ingredient having a health benefit, in this case in the prevention or treatment of allergic manifestations. By way of examples, the composition may be a fresh milk product of the yogurt type, a prepared meal, a sauce and the like. The composition may also be a product with a long shelf life, sterilized and/or dehydrated.

A composition obtained according to a preferred implementation of the invention is intended for infant nutrition. For example, it may be an infant milk (in dehydrated or nondehydrated form). A nonlimiting example of infant milk obtained in accordance with the present invention is the milk marketed under the name Gallia Calisma (1st or 2nd age) by the Danone group.

It is important to note that a composition obtained according to one of the above methods and in example 2 below may be incorporated, as ingredient, into any type of food composition. A food composition obtained according to the invention may therefore be characterized by the fact that it contains, as ingredient, at least one composition obtained according to one of the methods described above or in example 2 below. Such food compositions may be intended for human consumption or as animal feed and may be provided in particular in the form of a fermented or nonfermented, milk or nonmilk, preparation of animal or plant origin, including in particular infant formulas or formulas for adults and seniors, and in particular in the form of an infant milk preparation, liquid or powdered milk, fresh products, cereals, biscuits (filling), baby-food jars, desserts and the like, or alternatively in the form of food or dietary products for adults, including hospital products.

Alternatively, a composition obtained according to the present invention may be provided as a nutritional supplement.

According to another embodiment, the present invention relates to a method for preparing a pharmaceutical composition intended for the prevention and/or treatment of allergic manifestations. A pharmaceutical composition obtained according to the present invention will be characterized by the fact that it contains, as active ingredient, at least one composition obtained according to one of the methods described above or in example 2 below, and at least one pharmaceutically acceptable carrier. The expression "pharmaceutically acceptable" is understood to mean any carrier which, while preserving the properties of the composition obtained according to one of the methods described above or in example 2 below, makes it possible to carry said composition.

A nutritional supplement or a pharmaceutical composition obtained according to the present invention may be provided in any galenic form desired for oral administration to humans or animals, such as for example in liquid form for a syrup or a solution, a spray, or in solid form such as for example a powder, a tablet, a hard gelatin capsule, a soft gelatin capsule, a spray powder, a gum, a paste, granules, in their various forms, for immediate or programmed release, or in any other form suitable for oral administration. The pharmaceutical compositions obtained in accordance with the present invention may additionally be formulated for topical administration to humans or animals, for example in the form of a cream, a lotion, a soap, a solution, a gel, a milk, an oil or for anal administration to humans or animals, for example in the form of a suppository.

The compositions obtained by a method in accordance with the invention are preferably intended for human consumption, and will provide a benefit to anyone with an allergic predisposition. Individuals suffering from allergic-type manifestations, and neonates, breastfeeding infants or young children (up to 5 years) one of whose parents has an allergy and/or an atopic predisposition, constitute a population for whom these compositions will be of great benefit. Individuals suffering from food, respiratory or contact allergies, and atopic subjects, may also see an improvement in their condition as a result of regular consumption of a composition obtained by a method in accordance with the present invention.

The results of the study presented in the following examples below show in particular that infant preparations obtained in accordance with the invention make it possible, on the one hand, to prevent the appearance of a cow's milk protein allergy (CMPA) in a number of high allergic risk children and, on the other hand, to treat allergic-type skin manifestations in breastfeeding infants. The use of a *Bifidobacterium* strain, for the preparation of a composition intended for the prevention of cow's milk protein allergy and/or for the preparation of a composition intended for the prevention and treatment of allergic-type skin manifestations (eczema, desquamation, retroauricular fissure, erythema, itching and the like) in breastfeeding infants, therefore forms an integral part of the invention.

The present invention will be understood more clearly with the aid of the additional description which follows, which presents the antiallergic effects of the infant milk Gallia Calisma on breastfeeding infants having an allergic predisposition. Other preparations which can be used according to the present invention are also described.

EXAMPLES

Example 1

Antiallergic Effects of the Infant Milk Gallia Calisma

A preparation for infants (of the Calisma 1st age type) and a follow-on milk (of the Calisma 2nd age type) were incorporated into a prospective, longitudinal multicenter, randomized double blind study with 2 parallel groups. The method for preparing these compositions is schematically represented in FIG. 1.

The objective was to determine the efficiency of a bioconverted infant milk (FF) on the prevention of cow's milk protein allergy (CMPA), and the appearance of sensitization to allergens, in neonates and infants, compared with a nonbioconverted formula (SF).

High atopic risk children were recruited to participate in this study. The mothers were recruited before the 5th month of pregnancy, the child being monitored up to 12 months. The FF or SF were given from birth to 1 year or from weaning for breastfed children. Dietary monitoring was carried out from the 5th month of pregnancy and up to 12 months for the child with late diversification in accordance with current recommendations. During monitoring of the children during their first year, the manifestations compatible with a food allergy were recorded.

A systematic clinical examination was also performed at 4 and 12 months as well as prick-tests (skin tests which show sensitivity to a given allergen) for cow's milk (CM), soybean, egg, wheat, cod, peanut, *D. pteronyssinus*, *Alternaria*, cat, dog, and grass and birch pollen. In the event of CMPA being suspected, any intake of cow's milk proteins was interrupted and an oral provocation test (OPT) for CM was carried out.

Figure 2:
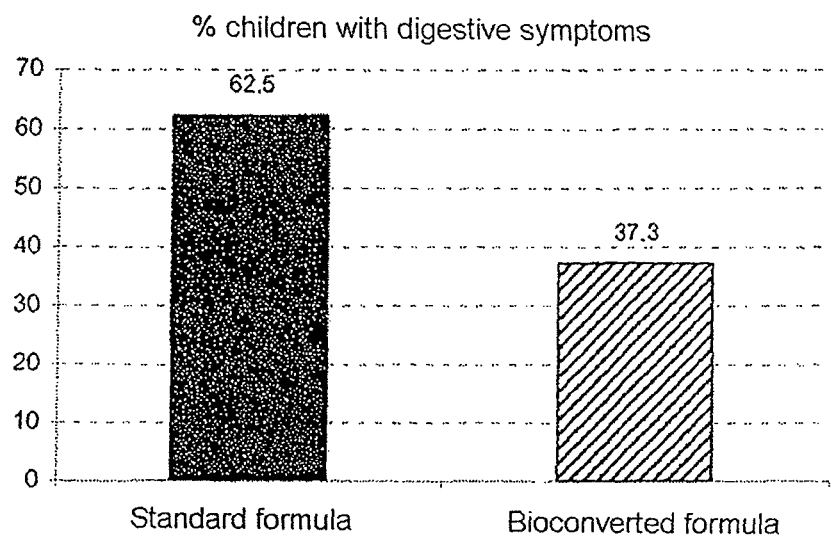
FIG. 2: Prevention of digestive allergic-type manifestations by a bioconverted formula. High atopic risk children were given either a standard formula (56 children) or a bioconverted formula (59 children), from birth to 1 year or from weaning for breastfed children. The percentage of digestive manifestations was observed at 12 months.
Figure 3:
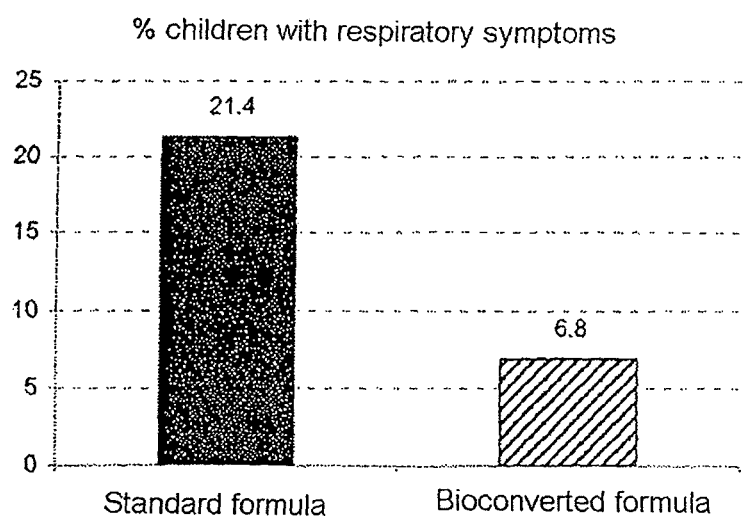
FIG. 3: Prevention of respiratory allergic-type manifestations by a bioconverted formula. High atopic risk children were given either a standard formula (56 children) or a bioconverted formula (59 children), from birth to 1 year or from weaning for breastfed children. The percentage of respiratory manifestations was observed at 12 months.

129 children were included, among whom 115 were monitored up to 12 months, of whom 59 consumed FF and 56 SF. Out of 115 patients, 83 presented symptoms compatible with a food allergy (72.2%). In the FF group, the percentage of digestive and respiratory manifestations observed is statistically lower than that for the SF group ($p<0.05$). These results are presented in FIGS. 2 and 3.

Figure 4:
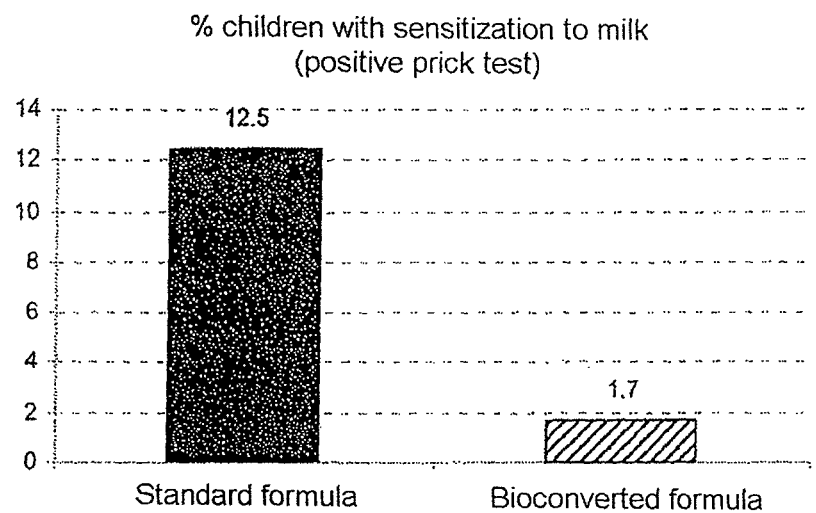
FIG. 4: Prevention of cow's milk protein allergy (CMPA) by a bioconverted formula. High atopic risk children were given either a standard formula (56 children) or a bioconverted formula (59 children), from birth to 1 year or from weaning for breastfed children. The percentage of children with sensitization to milk (positive Prick Test) was observed at 12 months.

Furthermore, for these 115 children, 7% showed sensitization to milk (positive Prick Test), with a significant difference ($p<0.05$) between the groups FF and SF (1.7% and 12.5% respectively) (FIG. 4).

This study has demonstrated for the first time the value of the use of a bioconverted formula in preventing the appearance of the manifestations of food allergy and of sensitization to cow's milk proteins.

FF was also tested during a prospective, longitudinal multicenter, open study evaluating the value of using such a formula in the management of minor skin symptomatology.

This study evaluated the effect of a specific bioconverted formula (Calisma), compared with a standard milk, by measuring the variation in minor skin manifestations in breastfeeding infants after replacing standard milk with the fermented formula.

Healthy infants, under 4 months old, showing allergic-type skin manifestations corresponding to a 1st symptomatological episode, were recruited. The skin manifestations revealed were the following: desquamation, retroauricular fissure, erythema, itching.

After consuming the bioconverted formula for one month, the variation in these minor skin manifestations (nature, location and intensity) was evaluated by a pediatrician or by the parents.

Figure 5:
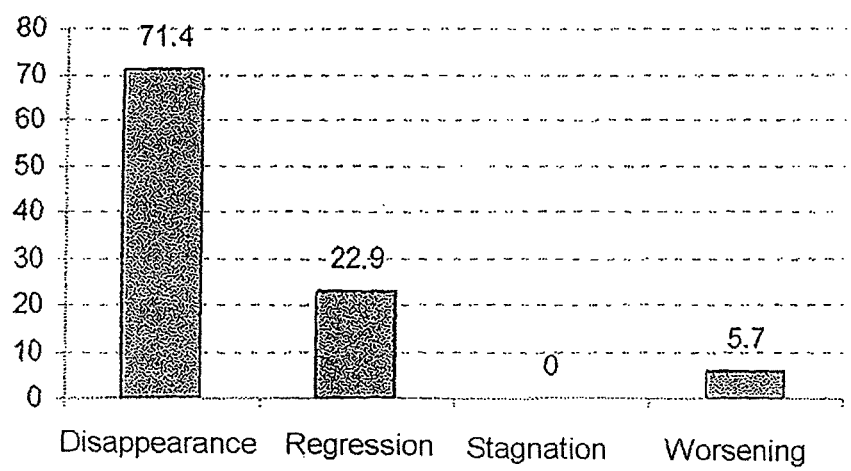
FIG. 5: Treatment of cutaneous allergic-type manifestations by a bioconverted formula. Thirty-five healthy breast-feeding infants, under 4 months old, showing allergic-type skin manifestations, were given the bioconverted formula for one month. The variation in the symptoms was then evaluated.

35 children were included in the study. After consuming the bioconverted formula for 1 month, a favorable variation in the manifestations was observed for 94% of the children, including a complete disappearance of the symptoms for 71% (FIG. 5).

These results show the efficiency of the product in the management of manifestations of an allergic nature.

Example 2

Preparation of Other Anti-Allergic Compositions

Other anti-allergic compositions may be obtained by a method comprising the following steps:
a—inoculation and incubation, under aerobic or anaerobic conditions and at a temperature of between 30 and 40° C. approximately, of *Bifidobacterium* comprising at least the *Bifidobacterium breve* I-2219 strain in an aqueous substrate having a pH of between 6 and 8 approximately, and comprising at least the following ingredients:
   i) whey permeate,
   ii) whey protein hydrolysate,
   iii) lactose
b—removal of the *Bifidobacterium* from the aqueous substrate;
c—ultrafiltration of the aqueous substrate on filtration membranes having a cut-off of between 100 and 300 kDa in order to obtain a concentrated retentate; supplemented, where appropriate, with steps d— and e— below:
d—dehydration of the concentrated retentate;
e—dissolution of the dehydrated retentate in a buffer.

Finally, the following steps f— and g— may be carried out in order to obtain active fractions from the retentate:
f—column gel exclusion chromatography having an exclusion threshold of 600 kDa of the solution of the retentate;
g—recovery of the excluded fraction and/or of the filtered fraction at the end of the chromatography.

More precisely, the products may be obtained using the protocol described below.

A culture medium containing the following ingredients is prepared:
50 g/l of whey permeate,
10 g/l of whey protein hydrolysate,
20 g/l of lactose,
2 g/l of yeast extract,
2.5 g/l of potassium dihydrogen phosphate,
0.3 g/l of cysteine hydrochloride
0.3 g/l of NaOH.

The culture medium is ultrafiltered on Centramate® cartridges sold by the company PALL, equipped with polyether sulfone membranes having a cut-off of 300 kDa and the permeate is autoclaved for 30 minutes at 120° C. The pH of the culture medium is then adjusted to a value of 6.5 with the aid of a half-diluted aqueous ammonia solution.

The culture medium is then inoculated with the bifidobacteria at the rate of 6‰ (v/v) of a frozen concentrate of the *Bifidobacterium breve* CNCM I-2219 strain containing $1.1 \times 10^{11}$ CFU of bifidobacteria per ml of frozen concentrate. The initial bacterial population is $3 \times 10^8$ CFU of bifidobacteria per ml of culture medium. The bifidobacteria are cultured under anaerobic conditions, at a temperature of between 35 and 40° C. During the culture, the pH of the culture medium is regulated at 6.5 by means of a half-diluted aqueous ammonia solution. The culture time is 15 hours, and the *Bifidobacterium* population at the end of the culture is about $2 \times 10^7$ CFU per ml of culture medium.

At the end of the culture, the bacteria are removed from the fermented culture medium by centrifugation for 1 hour at 3000 g. The residual enzymatic activities contained in the centrifugation supernatant are destroyed by heat treatment for 3 minutes at 75° C.

The supernatant is ultrafiltered on Centramate® cartridges sold by the company PALL, equipped with polyether sulfone membranes having a cut-off of 300 kDa at a temperature of 40° C. approximately. It is then concentrated 3-fold, and then washed 3 times with deionized water. During the last wash, the portion retained by the membrane is concentrated 7-fold. A concentrate called retentate is thus obtained. The retentate is dehydrated by lyophilization, and then taken up in a Tris-NaCl buffer at pH 8.

The concentrated retentate, taken up beforehand in a Tris-NaCl buffer pH 8, is subjected to preparative chromatography. The separation is carried out by chromatography on a Superdex® 200 gel column sold by the company Amersham Biosciences, having a diameter of 50 mm and a height of 100 cm, fed at a flow rate of 5 ml per minute and having an exclusion threshold of 600 kDa. The fractions are collected per 10 ml and their absorbance is measured at 280 nanometers.

Two fractions are thus separated:
a fraction excluded from the gel having a molecular weight greater than 600 kDa (retention time of 130 to 180 minutes +/−10%),
a filtered fraction having a molecular weight of between 200 and 600 kDa (retention time of 187 to 370 minutes +/−10%).

The excluded fraction is dialyzed against distilled water and then diluted so as to return to the concentration of the retentate. This fraction can then be stored in frozen or lyophilized form. The filtered fraction can also be stored in the same manner.

The retentate or any of the fractions separated by chromatography, as well as mixtures thereof, can be used to prevent, alleviate or treat allergic-type manifestations.

REFERENCES

Host, A., and Halken, S. (2005). Primary prevention of food allergy in infants who are at risk. Curr Opin Allergy Clin Immunol 5, 255-259.

Host, A., Koletzko, B., Dreborg, S., Muraro, A., Wahn, U., Aggett, P., Bresson, J. L., Hernell, O., Lafeber, H., Michaelsen, K. F., et al. (1999). Dietary products used in infants for treatment and prevention of food allergy. Joint Statement of the European Society for Paediatric Allergology and Clinical Immunology (ESPACI) Committee on Hypoallergenic Formulas and the European Society for Paediatric Gastroenterology, Hepatology and Nutrition (ESPGHAN) Committee on Nutrition, Arch Dis Child 81, 80-84.

Johansson, S. G., Hourihane, J. O., Bousquet, J., Bruijnzeel-Koomen, C., Dreborg, S., Haahtela, T., Kowalski, M. L., Mygind, N., Ring, J., van Cauwenberge, P., et al. (2001). A revised nomenclature for allergy. An EAACI position statement from the EAACI nomenclature task force. Allergy 56, 813-824.

Kalliomaki, M., Kirjavainen, P., Eerola, E., Kero, P., Salminen, S., and Isolauri, E. (2001). Distinct patterns of neonatal gut microflora in infants in whom atopy was and was not developing. J Allergy Clin Immunol 107, 129-134.

Osborn, D. A., and Sinn, J. (2006a). Formulas containing hydrolysed protein for prevention of allergy and food intolerance in infants. Cochrane Database Syst Rev, CD003664.

Osborn, D. A., and Sinn, J. (2006b). Soy formula for prevention of allergy and food intolerance in infants. Cochrane Database Syst Rev, CD003741.

Peng, S., Lin, J. Y., and Lin, M. Y. (2007). Antiallergic effect of milk fermented with lactic acid bacteria in a murine animal model. J Agric Food Chem 55, 5092-5096.

Prescott, S. L., Dunstan, J. A., Hale, J., Breckler, L., Lehmann, H., Weston, S., and Richmond, P. (2005). Clinical effects of probiotics are associated with increased interferon-gamma responses in very young children with atopic dermatitis, Clin Exp Allergy 35, 1557-1564.

Sudo, N., Sawamura, S., Tanaka, K., Aiba, Y., Kubo, C., and Koga, Y. (1997). The requirement of intestinal bacterial flora for the development of an IgE production system fully susceptible to oral tolerance induction. J Immunol 159, 1739-1745.

Terpend, K., Blaton, M. A., Candalh, C., Wal, J. M., Pochart, P., and Heyman, M. (1999). Intestinal barrier function and cow's milk sensitization in guinea pigs fed milk or fermented milk. J Pediatr Gastroenterol Nutr 28, 191-198.

The invention claimed is:

1. A method for the treatment of allergic manifestations in a child having an atopic disease or having a predisposition for atopic disease, comprising the step of administering to an infant with an allergic skin, respiratory, and/or digestive manifestation a composition containing a carrier prepared by a method comprising the step of bioconversion of a milk substrate with the aid of an in vitro culture of an isolated strain of *Bifidobacterium breve*, by maintaining said substrate in contact with said culture, under conditions unfavorable for the production of acid by said strain.

2. The method as claimed in claim 1, further comprising a step of fermenting a milk substrate in the presence of said *Bifidobacterium breve* strain to prepare said composition.

3. The method as claimed in claim 1, wherein the treatment of the allergic manifestations corresponds to the treatment of a cow's milk protein allergy in high allergy risk children and/or to the treatment of allergic-type skin manifestations in breastfeeding infants.

4. The method as claimed in claim 1, further comprising a step of fermenting a milk substrate in the presence of a *Streptococcus thermophilus* strain to prepare said composition.

5. The method as claims in claim 1, wherein the allergic skin manifestation is selected from the group consisting of: eczema, desquamation, retroauricular fissure, erythema, and itching.

* * * * *

UNITED STATES PATENT AND TRADEMARK OFFICE
CERTIFICATE OF CORRECTION

PATENT NO. : 9,707,258 B2  
APPLICATION NO. : 12/680779  
DATED : July 18, 2017  
INVENTOR(S) : Aubert-Jacquin et al.

Page 1 of 1

It is certified that error appears in the above-identified patent and that said Letters Patent is hereby corrected as shown below:

On the Title Page

Item [75], delete:
"Cécile Aubert-Jacquin, Lyons (FR):"

And insert:
--Cécile Aubert-Jacquin, Lyon (FR):--

Signed and Sealed this
Eighteenth Day of June, 2019

Andrei Iancu
*Director of the United States Patent and Trademark Office*